(12) United States Patent
Yamane et al.

(10) Patent No.: US 10,433,931 B2
(45) Date of Patent: Oct. 8, 2019

(54) DENTAL HANDPIECE NOZZLE

(71) Applicant: NAKANISHI INC., Kanuma-shi, Tochigi (JP)

(72) Inventors: Chihiro Yamane, Kanuma (JP); Shouichi Takamori, Kanuma (JP); Tetsuji Suzuki, Kanuma (JP); Kiyoshi Kawakubo, Kanuma (JP)

(73) Assignee: Nakanishi Inc., Kanuma-shi (JP)

( * ) Notice: Subject to any disclaimer, the term of this patent is extended or adjusted under 35 U.S.C. 154(b) by 0 days.

(21) Appl. No.: 14/772,612

(22) PCT Filed: Mar. 5, 2014

(86) PCT No.: PCT/JP2014/055657
§ 371 (c)(1),
(2) Date: Sep. 3, 2015

(87) PCT Pub. No.: WO2014/136847
PCT Pub. Date: Sep. 12, 2014

(65) Prior Publication Data
US 2016/0000523 A1 Jan. 7, 2016

(30) Foreign Application Priority Data
Mar. 7, 2013 (JP) .................... 2013-045879

(51) Int. Cl.
*A61C 3/00* (2006.01)
*A61C 3/025* (2006.01)
(Continued)

(52) U.S. Cl.
CPC ............. *A61C 3/025* (2013.01); *A61C 1/087* (2013.01); *A61C 17/0202* (2013.01);
(Continued)

(58) Field of Classification Search
CPC ..... A61C 3/025; A61C 1/087; A61C 17/0202; A61C 17/022
(Continued)

(56) References Cited

U.S. PATENT DOCUMENTS 4,276,880 A * 7/1981 Malmin ............. A61C 17/0202
433/80
5,857,851 A 1/1999 Chavanne
(Continued)

FOREIGN PATENT DOCUMENTS

| JP | 2002-165806 A | 6/2002 | |
| WO | WO 2011057008 A2 * | 5/2011 | ......... A61C 17/0208 |
| WO | WO 2011154718 A1 * | 12/2011 | ......... A61C 17/0202 |

*Primary Examiner* — Nicholas D Lucchesi
(74) *Attorney, Agent, or Firm* — Jason D. Voight

(57) ABSTRACT

A nozzle for a dental handpiece having a connector portion to be connected to a handpiece body, and a nozzle body, which is provided near its end with a notch of a substantially rectangular section cut out from the front face into the lateral faces, the notch forming upstream and downstream faces. The nozzle has a channel and an injection port thereof for transferring the mixture and a channel and an injection port thereof for transferring water, separate from each other. The channel for the mixture extends through the nozzle body along the front face from the connector portion to near the end, with the injection port for the mixture opened in the upstream face. With this nozzle, the mixture is properly injected onto a treatment site in subgingival treatment, while the mixture injected subgingivally is efficiently discharged supragingivally, to improve work efficiency in dental treatment.

3 Claims, 5 Drawing Sheets

(51) Int. Cl.
     *A61C 17/02*     (2006.01)
     *B05B 1/26*     (2006.01)
     *B24C 5/04*     (2006.01)
     *A61C 1/08*     (2006.01)
     *A61C 17/022*     (2006.01)

(52) U.S. Cl.
     CPC ............ *A61C 17/022* (2013.01); *B05B 1/267* (2013.01); *B24C 5/04* (2013.01)

(58) Field of Classification Search
     USPC ........................ 433/80, 91–96; 222/566–574
     See application file for complete search history.

(56) References Cited

U.S. PATENT DOCUMENTS

| | | | |
|---|---|---|---|
| 2004/0202980 A1 | 10/2004 | Policicchio | |
| 2006/0156463 A1* | 7/2006 | Kitano | B05B 15/70 |
| | | | 4/420.4 |
| 2007/0042316 A1 | 2/2007 | Pichat et al. | |
| 2008/0145814 A1 | 6/2008 | Pichat et al. | |
| 2010/0167233 A1* | 7/2010 | Dricot | A61C 1/0061 |
| | | | 433/82 |
| 2011/0117517 A1* | 5/2011 | Bergheim | A61C 5/02 |
| | | | 433/81 |
| 2013/0266908 A1* | 10/2013 | Casabonne | A61C 3/025 |
| | | | 433/88 |

\* cited by examiner

DENTAL HANDPIECE NOZZLE

This is the national stage of International Application PCT/JP2014/055657, filed Mar. 5, 2014.

FIELD OF ART

The present invention relates to a nozzle for a dental handpiece, in particular, a nozzle for a dental handpiece of a type wherein a nozzle is attached to a handpiece body at its nozzle connection port for injection of a mixture of air and powder together with water.

BACKGROUND ART

Dental handpieces are known, which mix air and powder for polishing or cleaning tooth surface, and inject the mixture together with water onto the tooth surface. Dental handpieces of this type are known, for example, from Patent Publication 1, wherein the dental handpiece is composed of a handpiece body and a nozzle. The handpiece body has a container for accommodating powder, an air supply line for supplying air into the container, a mixture transfer line for transferring a mixture of the powder and air to a nozzle, a water supply line for transferring water to the nozzle, and a head (nozzle connector portion) on which the nozzle is attached. The nozzle has a line and an injection port for each of the mixture and the water for separate injection thereof. The nozzle is inserted onto and fit on the head at the tip of the handpiece body, so that the line and the injection port for each of the mixture and the water through the nozzle are brought into communication with the corresponding mixture transfer line and water supply line in the handpiece body. In this way, the mixture of air and powder supplied through the handpiece body is adapted to be injected together with water through the nozzle.

As a nozzle for injecting a mixture of air and powder together with water, there is known a nozzle for use in subgingival treatment, such as disclosed in Patent Publication 2. As disclosed in this publication, a nozzle for subgingival treatment has a connector portion connected to a handpiece body, and a nozzle body extending from the connector portion toward the end, gradually tapering into a thin and flat form. Through the nozzle body, a channel for transferring a mixture of air and powder and a channel for transferring water are separately provided, extending from the connector portion toward the end of the nozzle body, and a mixture injection port and a water injection port for separately injecting the mixture and water are respectively opened in the end of the nozzle body. Examples of a commercial product that are in practical use for general dental or medical institutions include a nozzle entirely made of a resin and 1.62 mm wide and 0.78 mm thick in its end, or a nozzle entirely made of metal and 1.95 mm wide and 0.91 mm thick in its end.

These nozzles are connected to the nozzle connector port of the handpiece body by means of various securing means, such as of an insertion or screwing type, so as to transfer water and the mixture of air and powder supplied through the handpiece body through the lines in the nozzle respectively assigned to the water and the mixture, for injection through the respective injection ports during subgingival treatment, as discussed above.

Patent Publication 1: JP-H10-286268-A
Patent Publication 2: JP-2008-149138-A

SUMMARY OF THE INVENTION

The nozzles of this type for use in the subgingival treatment are, as discussed above, formed thin and flat, and the mixture channel and the water channel formed through the nozzle are respectively opened in the nozzle end to form a mixture injection port and a water injection port. With such a structure, when a user inserts the nozzle into a tiny gap between the subgingival tooth surface and the gum for injecting the mixture of air and powder, it is difficult for the user to aim the mixture injection port at a treatment site and to properly injecting the mixture onto a treatment site.

With a nozzle of such a structure, the injection ports in the nozzle end are caught between the subgingival tooth surface and the gum, which makes it difficult for the mixture injected through the injection ports to leave the subgingival area and to be efficiently discharged supragingivally.

The present invention aims to solve such problems of the prior art. It is an object of the present invention to provide a nozzle for a dental handpiece of this type, wherein the nozzle, when inserted into a tiny gap between the subgingival tooth surface and the gum for injection of a mixture of air and powder in subgingival treatment, may properly inject the mixture onto a treatment site, and efficiently discharge supragingivally the mixture injected subgingivally, to thereby improve work efficiency in dental treatment.

For achieving the above object, according to the present invention, there is provided a nozzle for a dental handpiece, wherein said nozzle is to be connected to a handpiece body for injection, together with water, of a mixture of air and powder supplied through the handpiece body, said nozzle comprising:

a connector portion to be connected to a handpiece body, and a nozzle body extending from said connector portion and having a front face, a rear face, two lateral faces, and an end, said nozzle body being provided near said end with a notch of a substantially rectangular section cut out from said front face into said lateral faces, said notch forming an upstream face and a downstream face, wherein said nozzle has a channel and an injection port thereof for transferring the mixture and a channel and an injection port thereof for transferring water, separate from each other, said channel for the mixture extending through the nozzle body along the front face from said connector portion to near said end, with said injection port for the mixture opened in said upstream face, and wherein said downstream face is provided with a guide for receiving the mixture injected through the injection port for the mixture and guiding said injected mixture outside the notch.

It is preferred that said upstream face and said downstream face are formed as slanted faces at an angle with respect to each other, flaring from inside to outside of the nozzle body, that said upstream face forms a guide face for allowing the mixture injected through the injection port to flow toward said connector portion, and that said downstream face forms a guide face for guiding the mixture injected through the injection port beyond the notch.

It is also preferred that the nozzle body is provided in at least one of said lateral faces a guide extending from said notch or a location near said notch to near said connector portion for allowing the mixture injected through the injection port for the mixture to flow toward the connector portion.

It is also preferred that said channel for water extends through the nozzle body along said rear face from said connector portion to said end, with said injection port for water being opened in said end.

In the nozzle for a dental handpiece according to the present invention, the mixture injection port is opened in the upstream face of the nozzle, while the guide for receiving the mixture injected through the mixture injection port and guiding the injected mixture outside the notch is provided on the downstream face of the nozzle. Thus, when inserting the nozzle into a tiny gap between the subgingival tooth surface and the gum for injecting the mixture of air and powder in subgingival treatment, a user may easily aid the mixture injection port at a treatment site, and properly inject the mixture onto the treatment site, which improves work efficiency in dental treatment.

Further, in the nozzle of the present invention, the upstream face and the downstream face are formed as slanted faces at an angle with respect to each other, flaring from the inside to the outside of the nozzle body, the upstream face forms a guide face for allowing the mixture injected through the injection port to flow tangentially, and a guide extending from the notch or a location near the notch to near the connector portion is provided in at least one of the lateral faces of the nozzle for allowing the mixture injected through the mixture injection port to flow tangentially. Thus, the mixture injected subgingivally may be guided supragingivally and discharged efficiently, which improves work efficiency in dental treatment.

BRIEF DESCRIPTION OF THE DRAWINGS

FIG. 4 shows partially-enlarged perspective views of the nozzle of the handpiece of FIG. 1, particularly the injection ports for the mixture and water, wherein FIG. 4(a) is a view seen from the front side of the nozzle, and FIG. 4(b) is a view seen from the rear side of the nozzle.

PREFERRED EMBODIMENTS OF THE INVENTION

Figure 1:
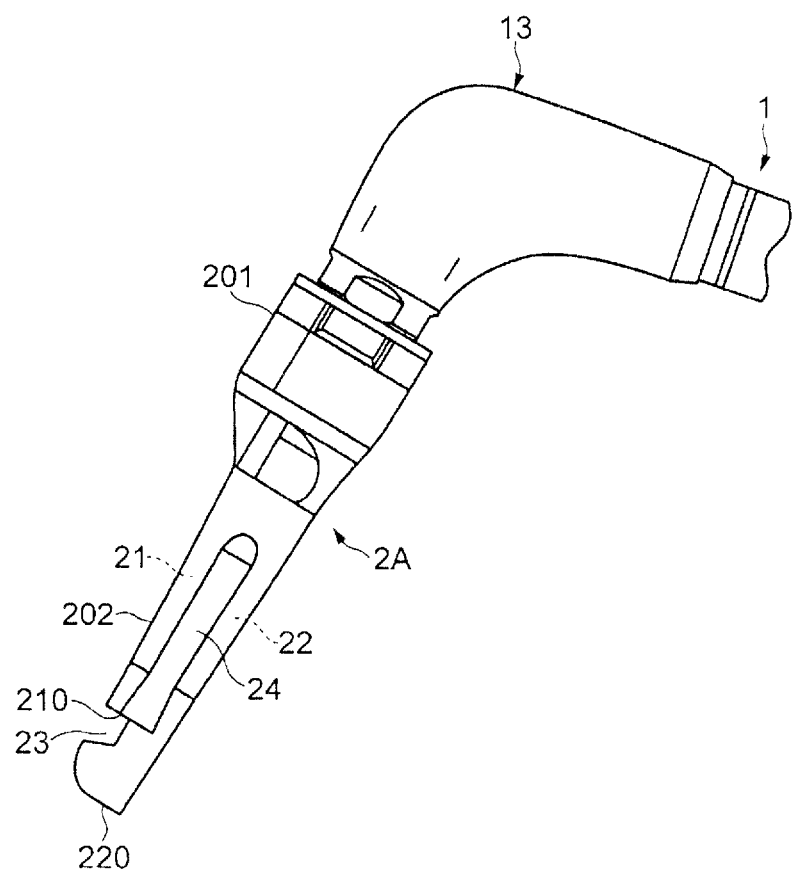
FIG. 1 is a side view of the first embodiment of the nozzle for a dental handpiece according to the present invention, with the main section of the handpiece body.
Figure 2:
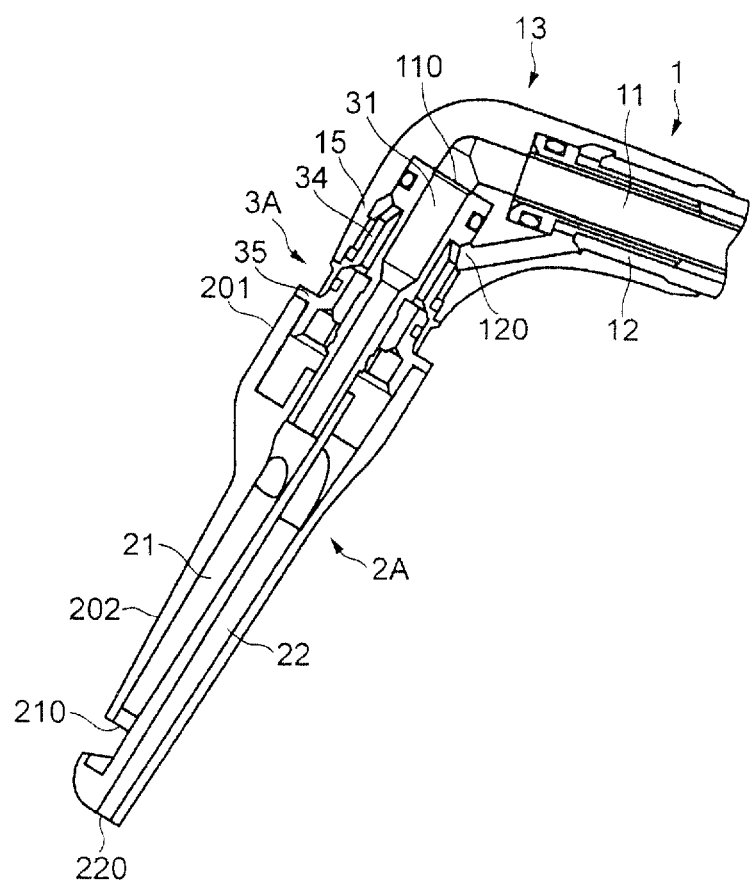
FIG. 2 is a side sectional view showing the structure of the nozzle of FIG. 1 with the main section of the handpiece body.
Figure 3:
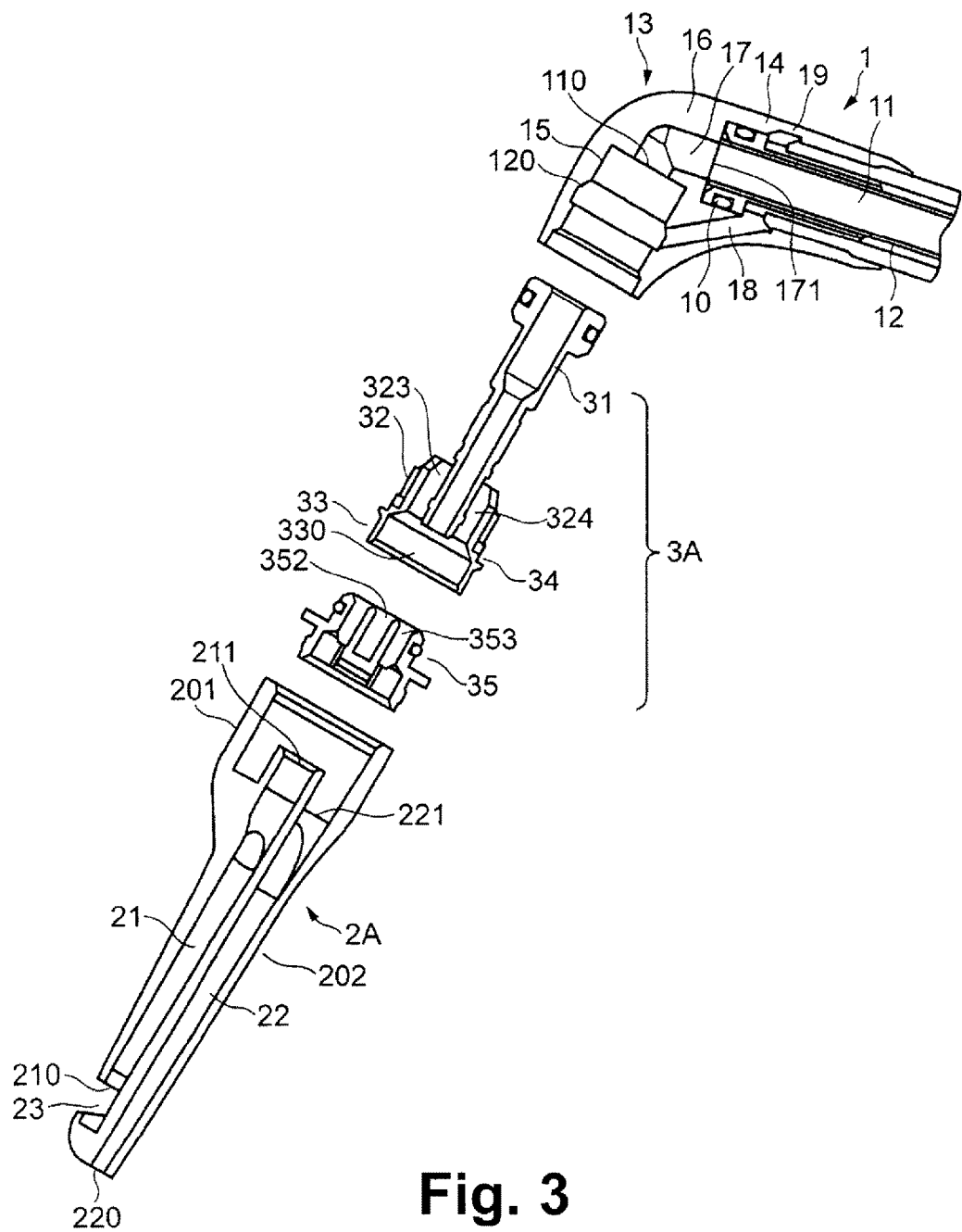
FIG. 3 is an exploded side sectional view showing the structures of various parts of the nozzle of FIG. 1 with the main section of the handpiece body.

The present invention will now be explained in detail with reference to the attached drawings. Referring to FIGS. 1 and 2, handpiece body 1 to which the nozzle of the present invention is connected has mixture transfer line 11 and outlet 110 thereof for transferring a mixture of air and powder, and water transfer line 12 and outlet 120 thereof for transferring water. The mixture transfer line 11 is arranged along the central axis of the handpiece body, and the water transfer line 12 is arranged around the mixture transfer line to form a double tube. The handpiece body 1 has head 13 at an end. As shown in FIG. 3, the head 13 is composed of a substantially L-shaped pipe, and has upstream connection port 14 for connection to the mixture transfer line 11 and the water transfer line 12, and downstream nozzle connection port 15 for connection to the nozzle. The head 13 further has blocking part 16 in the middle between the connection ports 14 and 15 for blocking. Through substantially the center of the blocking part 16, line 17 for the mixture extends to form part of the mixture transfer line 11, which line has inlet 171 communicating to the mixture transfer line 11 and the outlet 110 communicating to the nozzle connection port 15. The blocking part 16 is also provided with line 18 for water extending therethrough and offset from the line 17 for the mixture, forming part of the water transfer line 12. The water line 18 connects water channel 19 formed as a circumferential groove in the inner surface of the upstream connection port 14 and the outlet 120 of the water transfer line formed as a circumferential groove in the inner surface of the nozzle connection port 15, into communication at respectively predetermined axial positions. O-ring 10 is disposed in the upstream connection port 14 to make the head 13 water-tight with respect to the water transfer line 12.

As shown in FIGS. 1 and 2, nozzle 2A according to an embodiment of the present invention has connector portion 201 to be connected to the handpiece body 1, and nozzle body 202 contiguously extending from the connector portion 201 and having a front face, a rear face, two lateral faces, and an end. The nozzle 2A has channel 21 and injection port 210 thereof for transferring the mixture of air and powder, and channel 22 and injection port 220 thereof for transferring water, independent from each other, and adapted to be connected to the handpiece body 1 for injection therethrough water and the mixture of air and powder supplied through the handpiece body 1.

The nozzle 2A is for use in subgingival treatment, and the connector portion 201 is shaped corresponding to the nozzle connection port 15 in the end of the head 13 of the handpiece body 1, and the nozzle body 202 is formed thin and flat so as to be insertable between the tooth surface and the gingival margin. As shown in FIG. 3, the connector portion 201 is generally in a cylindrical form with an axial dent, and is provided with mixture inlet 211 for passing the mixture substantially in the center of the bottom of the axial dent, and with water inlet 221 for passing water around the mixture inlet 211. The nozzle body 202 is formed thin and flat such that the external width and thickness are gradually tapered from the connector portion 201, and in this embodiment in particular, formed flat in the transverse direction.

Figure 4:
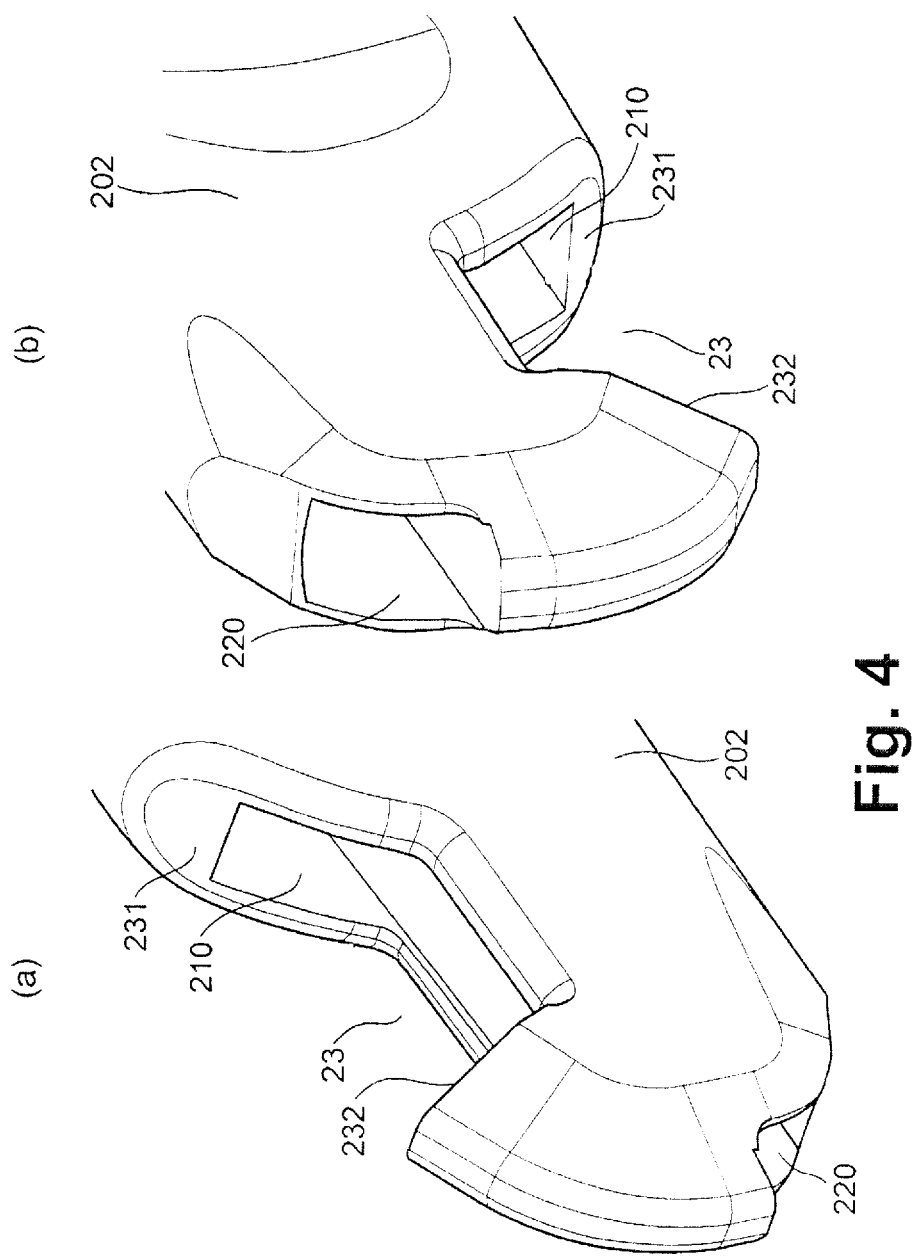

Near the end of the nozzle body 202, notch 23 of a substantially rectangular section is cut out from the front face into both lateral faces of the nozzle body 202, forming upstream face 231 and downstream face 232. As shown in FIG. 4, the upstream face 231 and the downstream face 232 of the notch 23 are formed as slanted faces at an appropriate angle with respect to each other, flaring from the inside to the outside of the nozzle body 202. The channel 21 for the mixture extends linearly in the axial direction through the nozzle body 202 along the front face from the inlet 211 located in the connector portion 201 down to near the end, and ends in the injection port 210 opened in the notch 23, in particular in the upstream face 231, as an outlet. The upstream face 231 functions as a guide for allowing the mixture injected through the injection port 210 to flow toward the connector portion 201, i.e., supragingivally, whereas the downstream face 232 functions as a guide for receiving and guiding the mixture injected through the injection port 210 beyond the notch 23.

Referring again to FIG. 1, in at least one of the lateral faces, preferably in each of the lateral faces of the nozzle body 202, groove 24 of a semicircular section is formed extending axially from a location near the notch 23 toward the connector portion 201, and functions as a guide for allowing the mixture injected through the injection port 210 to flow toward the connector portion 201, i.e., supragingivally.

The water channel 22 extends axially through the nozzle along the rear face from the water inlet 221 located in the connector portion 201, and ends in the injection port 220 opened in the end face of the nozzle body 202 as an outlet.

The nozzle 2A of such a structure is rotatably connected to the nozzle connection port 15 in the handpiece body 1 via rotary means 3A of a novel structure. As shown in FIG. 1, the rotary means 3A includes tubular member 31 which is rotatably arranged at its upstream end in the nozzle connection port 15 in the head 13 of the handpiece body 1, and fixed at its downstream end to the mixture channel 21 in the nozzle 2A; mounting member 34 fixed in the nozzle connection port 15 and rotatably receiving the tubular member 31 therethrough; and nozzle attachment 35 fixed in the connector portion 201 of the nozzle 2A and rotatably receiving the tubular member 31 therethrough. The tubular member 31 is rotatably arranged in the nozzle connection port 15, brought into communication with the outlet 110 of the mixture transfer line, and extends out of the nozzle connection port 15. The mounting member 34 is composed of annular fixing portion 2 fixed in the nozzle connection port 15, and annular guide portion 33 continuously and integrally formed with the fixing portion 32. The fixing portion 32 has tubular member receiving portion 323 in the center for rotatably receiving the tubular member 31, and water channel 324 around the portion 323 for communication with the outlet 120 of the water transfer line for water passage. The guide portion 33 is in an annular form, and has hollow 330 for guiding water from the water channel 324 of the fixing portion 32. The fixing portion 32 of the mounting member 34 having the structure as discussed above is fixed in the nozzle connection port 15, while the guide portion 33 is arranged outside the nozzle connection port 15. The tubular member 31 is rotatably inserted through the tubular member receiving portion 323 of the fixing portion 32 and the hollow 330 of the guide portion 33, and water is passed through the water channel 324 in the fixing portion 32 and the hollow 330 of the guide portion 33. The nozzle attachment 35 on its upstream side is rotatably arranged in the guide portion 33 of the mounting member 34, and on its downstream side is fixedly fit in the connector portion 201 of the nozzle 2A. The nozzle attachment 35 has tubular member receiving portion 352 in the center for rotatably receiving the tubular member 31 therein to bring the mixture channel 21 in the nozzle 2A into communication with the tubular member receiving portion 323 of the mounting member 34, and water channel 353 around the portion 352 for bringing the water channel 22 in the nozzle 2A into communication with the water channel 324 of the mounting member 34.

With such rotary means 3A, in the nozzle connecting port 15 in the head 13 of the handpiece body 1, the mounting member 34 is fixed, in the guide portion 33 of which the nozzle attachment 35 fixedly fit in the nozzle 2A is fit, and the tubular member 31 is fixedly connected to the mixture channel 21 in the nozzle 2A through the tubular member receiving portion 323 of the mounting member 34 and the tubular member receiving portion 352 of the nozzle attachment 35, to thereby connect rotatably the nozzle 2A to the handpiece body.

In this way, the tubular member 31, which is brought into communication with the outlet 110 of the mixture transfer line in the nozzle connection port 15 in the head 13 of the handpiece body, extends out of the nozzle connection port 15 and is rotatably supported through the mounting member 34, which is fixed in the nozzle connection port 15 and has the water channel 324 communicating with the outlet 120 of the water transfer line. The tubular member 31 is further brought into communication with and connected, via the nozzle attachment 35, to the mixture channel 21 in the nozzle 2A, and the nozzle attachment 35 fixed to the nozzle 2A is rotatably arranged in the guide portion 33 of the mounting member 34. With this structure, the tubular member 31 forms part of the circuit for introducing the mixture into the mixture channel 21 in the nozzle 2A, whereas the water channels 324 and 353 in the mounting member 34 and the nozzle attachment 35, respectively, arranged around the tubular member 31 form part of the circuit for introducing water into the water channel 22 in the nozzle 2A, so that the circuit for the mixture and the circuit for water are formed independently from each other. The tubular member 31, the nozzle attachment 35, and the nozzle 2A are integrally rotated around one of the two circuits, the tubular member 31, under the rotational guidance of the guide portion 33 of the mounting member 34 and the nozzle attachment 35.

In this way, the nozzle 2A is rotatable independently with respect to the head 13 of the handpiece body 1. Thus, when moved along the tooth surface, the nozzle 2A may be adjusted to an appropriate angle with respect to the tooth surface by rotation.

Figure 5:
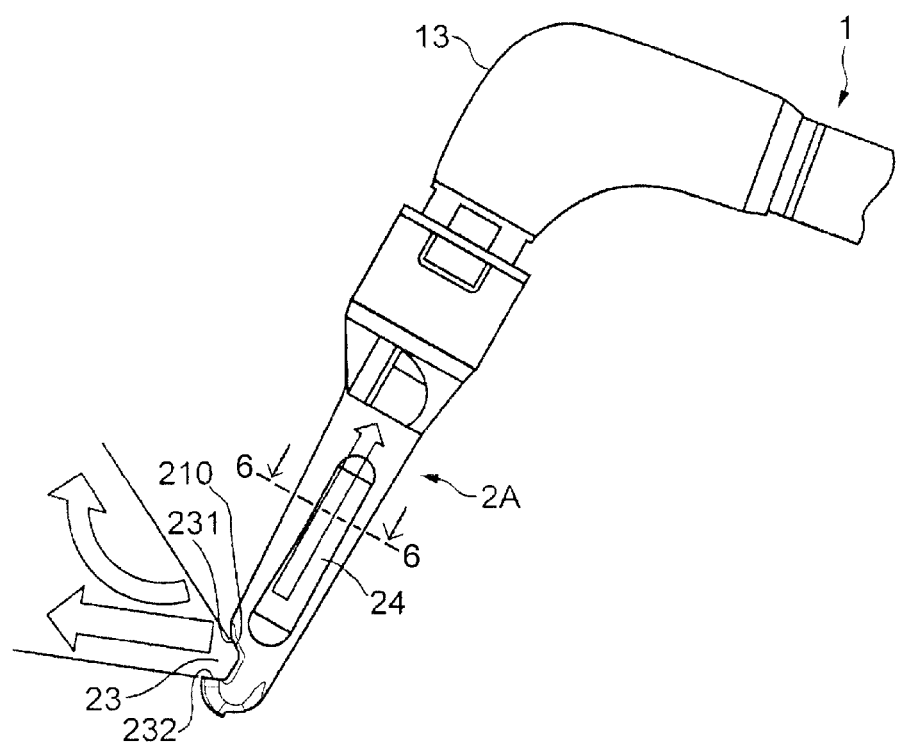
FIG. 5 shows the flow of the mixture injected through the nozzle of FIG. 1.
Figure 6:
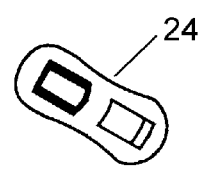
FIG. 6 shows an enlarged sectional view along line 6-6 in FIG. 5.

With the nozzle 2A for a dental handpiece, the mixture of air and powder supplied through the mixture transfer line 11 in the handpiece body 1 is injected from the outlet 110 of the mixture transfer line in the head 13, via the mixture channel 21 in the nozzle 2A, out of the mixture injection port 210 of the nozzle 2A. On the other hand, the water supplied through the water transfer line 12 in the handpiece body 1 is injected from the outlet 120 of the water transfer line in the head 13, via the water channel 324 in the fixing portion 32 of the mounting member 34, the water channel 353 in the nozzle attachment 35 arranged in the guide portion 33, and the water channel 22 in the nozzle 2A, out of the water injection port 220 of the nozzle 2A. As shown in FIG. 5, the mixture injected through the mixture injection port 210 of the nozzle 2A is blown beyond the notch 23 under the guidance of the downstream slant face 232 of the notch 23 facing to the injection port 210, to ensure that the mixture is blown onto a particular area of the treatment site. The mixture injected through the mixture injection port 210 of the nozzle 2A is also ensured to flow supragingivally under the guidance of the upstream slant face 231 of the notch 23, in which the injection port 210 is opened, as well as the grooves 24 on both lateral faces of the nozzle 2A.

As discussed above, the user, when moving the nozzle 2A along the tooth surface at a treatment site, with the end of the nozzle 2A inserted subgingivally, may easily adjust the nozzle 2A at an appropriate angle with respect to the tooth surface at a treatment site by rotating the nozzle 2A, to ensure that the mixture injected through the nozzle 2A is blown onto the tooth surface at a treatment site. Further, the mixture injected through the mixture injection port 210 may be ensured to be blown onto a particular area of the tooth surface at a treatment site under the guidance of the downstream face 232 facing to the injection port 210. The mixture injected through the mixture injection port 210 is also ensured to flow supragingivally under the guidance of the upstream face 231, in which the injection port 210 is opened, as well as the grooves on both lateral faces of the nozzle 2A.

Therefore, with the nozzle 2A, the nozzle may be inserted into a tiny gap between the subgingival tooth surface and the gum for properly injecting the mixture of air and powder toward a treatment site in subgingival treatment, while the mixture injected subgingivally may efficiently be discharged supragingivally, to thereby improve work efficiency in dental treatment.

Incidentally, while in this embodiment, the nozzle 2A has been described as an example to be rotatably connected to the handpiece body 1 by means of rotary means 3A composed of the tubular member 31, the mounting member 34, and the nozzle attachment 35, the nozzle may be connected to the handpiece body by means of other rotary means or, in the alternative, may be non-rotatably fixed to the handpiece body, and the connection to the handpiece body may be changed variously.

DESCRIPTION OF REFERENCE SIGNS 1 handpiece body
10 O-ring
11 mixture transfer line
110 outlet of mixture transfer line
12 water transfer line
120 outlet of water transfer line
13 head
14 upstream connection port
15 nozzle connection port
16 blocking part
17 line for mixture
171 inlet
18 line for water
19 water channel
2A nozzle
201 connector portion
202 nozzle body
21 channel for mixture
210 injection port for mixture
211 inlet for mixture
22 water channel
220 injection port for water
221 inlet for water
23 notch
231 upstream slant face
232 downstream slant face
24 groove
3A rotary means
31 tubular member
32 fixing portion
323 tubular member receiving portion
324 water channel
33 guide portion
330 hollow
34 mounting member
35 nozzle attachment
352 tubular member receiving portion
353 water channel
2B nozzle
204 axial dent

What is claimed is:

1. A nozzle for a dental handpiece, wherein said nozzle is to be connected to a handpiece body for injection, together with water, of a mixture of air and powder supplied through the handpiece body, said nozzle comprising:
   a connector portion to be connected to a handpiece body, and
   a nozzle body extending from said connector portion and having a front face, a rear face, two lateral faces, and an end, said nozzle body being formed thin and flat in a transverse direction so that said front and rear faces are narrower than said two lateral faces, said nozzle body being provided near said end with a notch of a substantially rectangular section cut out from said front face into said lateral faces, said notch forming an upstream face and a downstream face,
   wherein said nozzle has a channel and an injection port thereof for transferring the mixture and a channel and an injection port thereof for transferring water, separate from each other, said channel for the mixture extending linearly in an axial direction through the nozzle body along the front face from said connector portion to said injection port for the mixture near said end, with said injection port for the mixture opened in said upstream face,
   wherein said downstream face is provided with a guide for receiving the mixture injected through the injection port for the mixture and guiding said injected mixture outside the notch,
   wherein said upstream face and said downstream face are formed as slanted faces at an angle with respect to each other, flaring from inside to outside of the nozzle body toward the front face of the nozzle body,
   wherein said upstream face forms a guide face for guiding the mixture injected through the injection port to flow toward said connector portion, and
   wherein said downstream face forms a guide face for guiding the mixture injected through the injection port beyond the notch,
   wherein said nozzle body is provided in at least one of said lateral faces with a groove extending from said notch or a location near said notch to near said connector portion for guiding the mixture injected through the injection port for the mixture to flow toward the connector portion.

2. The nozzle for a dental handpiece according to claim 1, wherein said channel for water extends through the nozzle body along said rear face from said connector portion to said end, with said injection port for water being opened in said end.

3. The nozzle for a dental handpiece according to claim 1, wherein said groove has a semicircular section.

* * * * *